US00PP12328P2

(12) United States Plant Patent
Matsukizono

(10) Patent No.: US PP12,328 P2
(45) Date of Patent: Jan. 1, 2002

(54) PORTULACA PLANT NAMED 'SUMMER JOY ORANGE'

(75) Inventor: Hiromi Matsukizono, Kagoshima (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/353,042

(22) Filed: Jul. 13, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,349 P * 4/2000 Babikow ..... Plt./263

* cited by examiner

*Primary Examiner*—Bruce R. Campell
*Assistant Examiner*—Wendy C Baker
(74) *Attorney, Agent, or Firm*—Rothwell, Figg, Ernst & Manbeck

(57) ABSTRACT

Portulaca 'Summer Joy Orange' is a new variety of *Portulaca oleracea*. This plant has a vigorous, spreading plant growth which produces large, orange flowers having a red center.

1 Drawing Sheet

BACKGROUND OF THE NEW PLANT

This invention relates to a new and distinct cultivar of Portulaca plant, hereinafter referred to by the name 'Summer Joy Orange'. Portulaca 'Summer Joy Orange' is a new variety of *Portulaca oleracea*. The plant has a vigorous spreading growth habit and can be used as a groundcover. It can also be used in a potted or hanging basket presentation. The invention's flowers are orange (RHS 24A) with a red (RHS 42A) center. The flowers are single and measure 5.1 to 5.6 centimeters in diameter when fully open. There are five distinct petals with an indent a the tip of each petal. Portulaca flowers will typically close under low light and low temperature conditions such as late in the day and at night. 'Summer Joy Orange' Portulaca flowers will stay open later into the evening than most other cultivated varieties. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Summer Joy Orange' has been reproduced by stem cuttings in Salinas, Calif., and all of the characteristics thereof have been determined to be firmly fixed.

'Summer Joy Orange' originated from a hybridization made by the inventor Hiromi Matsukizono in Japan. The female parent is a commercial variety known as 'Yubi® Apricot', an unpatented variety of Portulaca and the male parent was a commercial variety known as 'Yubi® Yellow'. The initial cross-pollination of the parents, resulting in $F_1$ generation seed, was made in June, 1991. In February, 1992, the $F_1$ seed was sown. From these plants, three plants were selected for appealing flower color. In June through September of 1992 the three selected plant lines were vegetatively propagated and tested for easy reproducibility and stability of traits. One of these three plant lines was hence selected for orange flower color, large flower size and easy propagation. In February, 1997, cuttings of this plant line were sent to California. During the spring and summer of 1997 and 1998, plants were grown under the direction and supervision of the inventor for evaluation of the stability of the line's desired traits. Plants were evaluated in greenhouse pots at the research station at Salinas, Calif., and at the breeding station in Kakegawa, Japan. The invention, 'Summer Joy Orange' Portulaca, was determined by the inventor to have its characteristics, as herein described, firmly fixed.

BRIEF DESCRIPTION OF DRAWINGS

The accompanying drawings serve by color photographic means to illustrate the new plant variety, 'Summer Joy Orange'. The colors are represented as true as possible using conventional photographic procedures.

DETAILED DESCRIPTION OF THE NEW VARIETY

Figure 1:
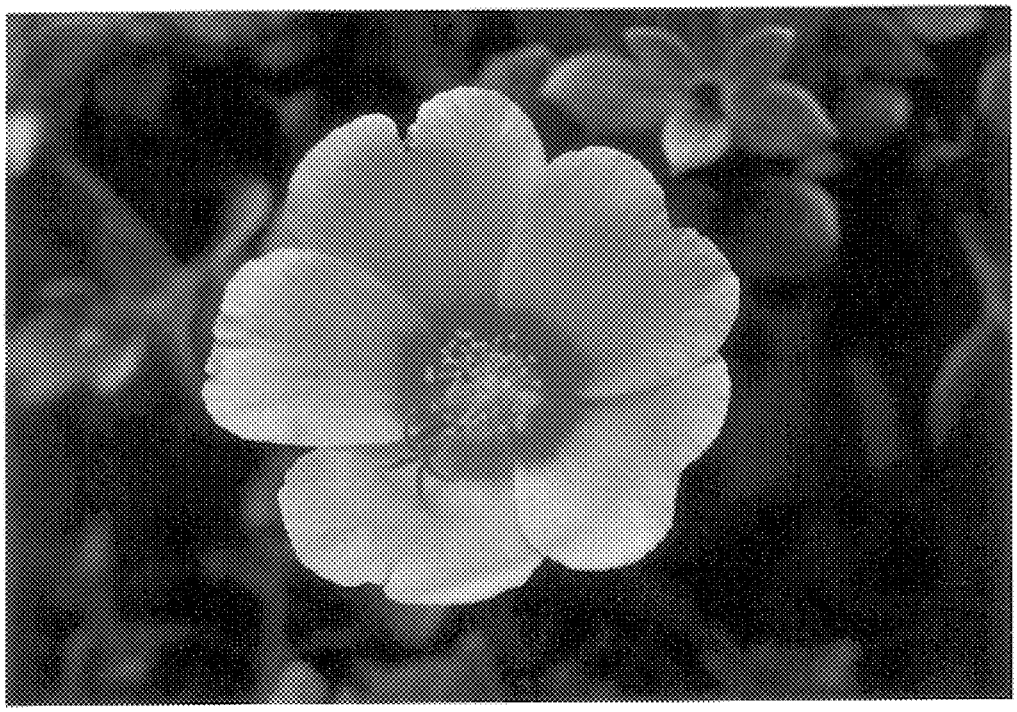
FIG. 1 is a close-up view of a 'Summer Joy Orange' flower illustrating its color and shape.
Figure 2:
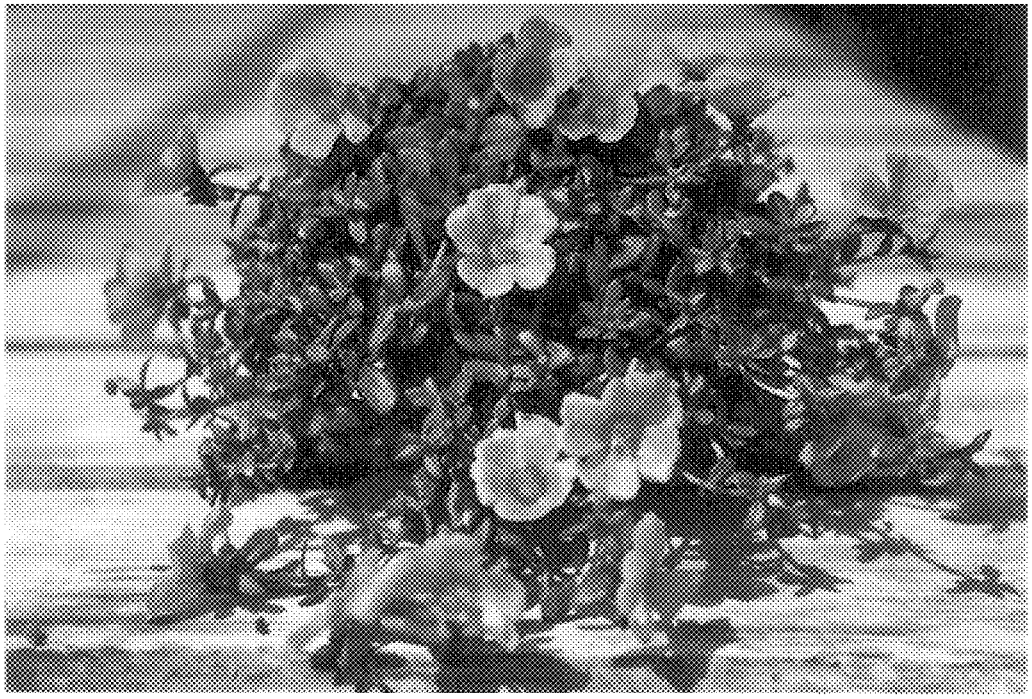
FIG. 2 is a view of the new cultivar after growing in a greenhouse for 8 to 10 weeks in a six-inch diameter pot.

The following description is based on observations and measurements from 14–16 week old plants grown in six-inch pots at Salinas, Calif. These plants were grown in plastic pots containing a peat moss-based medium. The plants were grown in the greenhouse under full sunlight in Salinas, Calif. Night temperatues ranged from 16° C. to 21° C. and day temperatures ranged from 24° C. to 35° C. The soil was not allowed to stay saturated but the plants were irrigated when the soil began to dry, or every second or third day. Soluble fertilizer was applied through an overhead irrigation system. The fertilizer contained 18% nitrogen, 8% phosphorus and 18% potassium. Every fourth irrigation was done with non-fertilizer water. Color designations were made according to The Royal Horticultural Society Colour Chart published by The Royal Horticultural Society of London, England.

Origin: Japan.
Parentage:

*Female parent.*—Yubi® Apricot (not patented).
*Male parent.*—Yubi® Yellow (not patented).

Classification:
*Family.*—Portulacaceae.
*Genus.*—Portulaca.
*Species.*—Oleracea.
*Commercial.*—Portulaca/Purslane 'Summer Joy Orange'.

Plant:
*Growth habit.*—Prostrate.
*Plant height.*—7 cm.
*Spreading area of plant.*—60–80 cm (in a six-inch pot).
*Vigor.*—The plant is most vigorous at high temperatures.
*Time to initiate/develop roots.*—Vegetative cuttings root in 7–10 days after placing into a rooting medium such as a peat moss-based mixture. The cuttings will form roots without the use of overhead mist.

Stem:
*Thickness.*—2.4 mm.
*Color.*—Yellowish green (146C) with red-purple (60A) anthocyanin pigment present in the axial portion of the stem.
*Pubescence.*—Present only at the nodes.
*Branching.*—Abundant.
*Length of Internode.*—5–15 mm.

Leaf:
*Shape.*—Oblanceolate with cuspidante tip in mature leaves and acute tips in younger leaves near the apex of the stem.
*Length* (*average*).—2.6 cm.
*Width* (*average*).—1.3 cm.
*Thickness.*—1.4 mm.
*Color.*—Upper leaf surface is green RHS 137A and the lower surface is green (137C) with red-purple (60A) anthocyanin present at the edge.
*Pubescence.*—None.
*Texture.*—Leaf surface is smooth, shiny and wax-like. Leaves are thick and fleshy.

Flower:
*Shape.*—Five distinct petals with an indent at tip of petal.
*Petal shape.*—Heart-shaped with a square base; approximately 1.7×1.8 cm.
*Lobation.*—None.
*Diameter.*—5.1–5.6 cm when fully opened.
*Color.*—Unopened stage (the development stage at which the petals have elongated from the sepals but not yet fully extended and opened): Orange (22A); Mature stage: Upper is orange (24A) with a center of red (42A); Lower is orange (24B).
*Bud.*—Lanceolate shaped; mature bud measures 1.6 cm in length and 0.7 cm in diameter; bud color is yellow-green (145A).
*Sepal.*—Two sepals; deltoid shaped; measures 1.0 cm in length and 0.9 cm in width; septals are thin, paper-like, smooth and shiny; sepals are translucent with green venation.
*Habit.*—The flowers bloom during midmorning and close at night. Each flower blooms only once. Flowers are produced throughout the growing season. The plants produce flowers regardless of day length. Plants can have 40 to 50 open flowers at one time. There is no fragrance.
*Season of bloom.*—In zone 9 and similar locations this plant will flower throughout the entire year. Growth is less vigorous during the cool temperatures and short days of winter, but the plant will continue to bloom.
*Hardiness.*—Plant is heat tolerant; thrives in heat and humidity; plant is not cold tolerant below 7° C.
*Reproductive organs.*—One orange-red (34A) pistil with five narrow style branches and many yellow (17C) stamen with orange-yellow anthers and red filaments; pollen is orange-red (34A); does not produce seed.

Disease and Insect Resistance

No unusual susceptibilty to diseases or insects have been observed.

Comparison with Other Known Varieties

The new variety is distinguished from other Portulaca plants known to inventor by its flower color, larger flower size and ability to stay open later into the evening. The closest commercial cultivar that we are aware of is the Portulaca plant named 'Yubi® Apricot' (an unpatented variety). The distinguishing characteristics, which differentiate 'Summer Joy Orange' from 'Yubi® Apricot', are:

| | 'Summer Joy Orange' | 'Yubi ® Apricot' |
|---|---|---|
| Flower Diameter | 5.1–5.6 cm | 4.2–4.7 cm |
| Flower Color | Orange with a red center | Lighter orange |
| Flower Closing Behavior | Open longer in evening | Closes earlier in afternoon |

We claim:

1. A new and distinct cultivar of Portulaca plant as shown and described herein.

* * * * *